United States Patent [19]
Zapf et al.

[11] Patent Number: 5,844,129
[45] Date of Patent: Dec. 1, 1998

[54] METHOD FOR DETERMINING THE MAGNETIC CONTAMINATION OF A SURFACE

[75] Inventors: Lothar Zapf, Alzenau; Wilhelm Fernengel, Kleinostheim; Klaus Rehbein, Hanau, all of Germany

[73] Assignee: Vacuumschmelze GmbH, Hanau, Germany

[21] Appl. No.: 746,906

[22] Filed: Nov. 19, 1996

[30] Foreign Application Priority Data

Dec. 1, 1995 [DE] Germany ............... 195 44 975.4

[51] Int. Cl.$^6$ ................................................. G01N 33/00
[52] U.S. Cl. ........................... 73/104; 73/865.8; 73/866
[58] Field of Search ............................. 73/104, 865.8, 73/866

[56] References Cited

U.S. PATENT DOCUMENTS 5,000,203  3/1991  Hamada ........................ 134/1

FOREIGN PATENT DOCUMENTS 5-346403  12/1993  Japan .
6-302691  10/1994  Japan .

*Primary Examiner*—Daniel S. Larkin
*Attorney, Agent, or Firm*—Hill & Simpson

[57] ABSTRACT

In the manufacture of magnetic data carriers, such for example, hard-disk storages, it must be assured that neither the data carrier itself nor component parts of the data carrier system situated in the proximity has magnetic contaminants. An improved measuring method allows the determination of the magnetic contaminants which were attached to an adhesive tape applied to the surface being examined. The improvement is that a magnetized soft-magnetic measuring substrate has a surface provided with a parting agent which is then brought into contact with the magnetic contaminants adhering to the adhesive tape. A reduction of the remanent field that is produced by this contact represents a criterion for the magnetic contamination of the surface under examination.

11 Claims, No Drawings

METHOD FOR DETERMINING THE MAGNETIC CONTAMINATION OF A SURFACE

BACKGROUND OF THE INVENTION

The present invention is directed to a measuring method for determining a magnetic contamination of a surface due to the adhering of magnetic particles thereon.

In the manufacture of magnetic data carriers or data carrier systems, for example hard-disk storages, any and all magnetic contamination, which, for example, can occur due to a superfine magnetic or magnetizable particles on construction parts or on work equipment that are used for manufacturing the data carriers, must be avoided. In particular, magnetizable contaminants on, for example, a hard disk modify the magnetic behavior of this disk so that either a correct registration of data is not possible or recorded data can no longer be read and is, thus, destroyed.

A dependable measuring method for a quick and exact determining of the degree of contamination of the surfaces is required in order to acquire the degree of contamination on component parts, assembly devices or surfaces. To accomplish this goal, it is standard to acquire the particles contaminating a surface by a method wherein an adhesive tape is glued to the surface and then removed, so that the particles that contaminate the surface cling to the adhesive tape. The adhesive tape is usually examined for magnetic particles in that the adhesive tape is metallized to make it electrically conductive and the particles can thus be recognized in a scanning electron microscope. The particles adhering to the defined area can then be counted with a scanning electron microscope. This method is extremely exact and acquires all particles. However, a reliable distinction cannot always be made between magnetizable particles and paramagnetic particles. Moreover, since a number of hours is usually required for the analysis, this method requires very long measuring times. Another disadvantage of the method is that the measuring equipment is extremely complicated and expensive.

SUMMARY OF THE INVENTION

The object of the present invention is to provide a method that allows a reliable measurement in a short time without involving specimen preparations and which utilizes significantly more cost-beneficial measuring apparatus.

To accomplish this goal, the present invention is directed to an improvement in a method of determining magnetic contaminants adhering to a surface, which method applies an adhesive tape to the surface being examined, removes the magnetic tape and then examines the tape to determine the number of adhering magnetic particles on the tape. The improvement comprises the step of examining being done by magnetizing a measuring substrate composed of a soft magnetic material, measuring the remanent magnetization of the measuring substrate to obtain a first value, providing a parting agent to one surface of the measuring substrate, placing the adhesive tape which is being examined in contact with the surface having the parting agent and moving the tape at least once over the surface, then, after removing the adhesive material, measuring the remanent magnetization of the measuring substrate to obtain a second value and comparing the second value with the first value obtained before contact with the adhesive tape to determine the magnetic contamination of the adhesive tape.

Other advantages and features of the invention will be readily apparent from the following description of the preferred embodiments and the claims.

DESCRIPTION OF THE PREFERRED EMBODIMENTS

In the present method, a measuring substrate of soft metallic material is first magnetized and then the remanent magnetization is measured to obtain a first value. This measuring substrate is advantageously composed of a disk-shaped or strip-shaped piece that, for example, can be a piece of a hard disk used in data storage. The magnetization preferably occurs perpendicular to the surface to be brought into contact with the adhesive tape, even though an effect would also occur given other directions of magnetization. The adhesive tape with the adhering contaminants, which were obtained from the surface under examination, is then pressed against the surface of the substrate of soft magnetic material, which surface had been previously provided with a parting agent, and the tape is moved back and forth thereon several times as a rule. A liquid or a mixture of a plurality of liquids that will wet the surface of the measuring substrate and prevent an adhesion of the adhesive tape, which is provided with contaminants, is preferably employed as the parting agent.

The magnetic and magnetizable particles are thereby magnetized by the magnetic field emerging from the measuring substrate. Given movement across the surface, the magnetizable particles influence the magnetic field of the measuring substrate. Since the measuring substrate is an adequately soft-magnetic material that has a low coercivity, the remanent magnetization of the measuring substrate is reduced by the presence of magnetic particles on the adhesive strip.

After the movement of the adhesive tape on the measuring substrate, the adhesive tape is then removed and the measuring substrate is measured in the same measuring apparatus, for example in a measuring unit with Förster probes of a magnetoscope or a flux gate magnetometer and the remanence is identified as a second value. The difference between the first value of remanence immediately after the magnetization of the measuring substrate and the second value obtained after the treatment with adhesive tape then represents a criterion for the contamination of the adhesive tape and, thus, of the surface under examination.

Since low magnetic fields are involved, disturbing magnetic fields from electromagnetic equipment in the proximity of the device or from passing vehicles as well could act on the measuring substrate and, thus, falsify the measured results. It is therefore especially advantageous to provide the measuring station with a shielding that is at least partially composed of a highly permeable soft-magnetic material, for example mu metal. As a result of this shielding, the measuring precision is additionally enhanced by a multiple compared to the measurement without such a shielding.

Although various minor modifications may be suggested by those versed in the art, it should be understood that we wish to embody within the scope of the patent granted hereon all such modifications as reasonably and properly come within the scope of our contribution to the art.

We claim:

1. In a measuring method for determining a magnetic contamination of a surface, said method applying an adhesive tape to a surface under examination, removing the adhesive tape, and examining the tape for adhering magnetic particles, the improvement comprising the step of examining the tape for adhering magnetic particles comprising providing a measuring substrate composed of soft-magnetic material, magnetizing said measuring substrate, measuring the remanent magnetization of the measuring substrate to obtain a first value, providing a surface of the measuring substrate with a parting agent, applying the adhesive tape for examination against said surface of the measuring substrate provided with the parting agent and moving the adhesive tape relative to the surface, then removing the adhesive tape, measuring the resulting remanent magnetization after removal of the tape to obtain a second value, and then comparing the second value to the first value to determine the magnetic contamination on the adhesive tape.

2. In a method according to claim 1, wherein the step of providing the measuring substrate provides a piece of hard-disk used for data storage.

3. In a method according to claim 1, wherein the step of measuring the magnetic remanence of the measuring substrate before and after treatment with adhesive tape utilizes a measuring station with a flux gate magnetometer.

4. In a method according to claim 3, which includes shielding the measuring station by a shielding housing for eliminating disturbing magnetic fields from the surroundings.

5. In a method according to claim 3, which includes providing a shielding for the measuring station, said shielding being at least partially composed of a highly permeable soft-magnetic material to increase the measuring precision.

6. In a method according to claim 1, wherein the step of applying a parting agent applies an agent selected from a group consisting of a liquid and a mixture of a plurality of liquids.

7. In a method according to claim 1, wherein the measuring substrate essentially has a flat surface of a disk shape or a strip shape.

8. In a method according to claim 7, wherein the measuring substrate is a piece of hard disk employed for data storage.

9. In a method according to claim 7, wherein the steps of measuring are accomplished in a measuring station having a measuring apparatus using a flux gate magnetometer.

10. In a method according to claim 7, which includes the step of surrounding the measuring station with a shield housing to eliminate disturbing magnetic fields from the surroundings.

11. In a method according to claim 7, which includes the step of providing a shielding for the measuring station, said shielding being at least partially composed of a highly permeable soft-magnetic material to improve the measuring precision.

* * * * *